United States Patent [19]

Wootton

[11] 4,246,273
[45] Jan. 20, 1981

[54] 1,5-DISUBSTITUTED IMIDAZOLID-4-ONES

[75] Inventor: Gordon Wootton, Sawbridgeworth, England

[73] Assignee: Beecham Group Limited, England

[21] Appl. No.: 24,190

[22] Filed: Mar. 27, 1979

[30] Foreign Application Priority Data

Mar. 30, 1978 [GB] United Kingdom ............ 12367/78
Oct. 13, 1978 [GB] United Kingdom ............ 40506/78

[51] Int. Cl.$^3$ ............... A61K 31/415; C07D 233/22
[52] U.S. Cl. ............... 424/273 R; 548/301;
548/309; 548/312; 548/313
[58] Field of Search ............... 548/320, 301; 424/273 R

[56] References Cited

U.S. PATENT DOCUMENTS

| 4,147,796 | 4/1979 | Wootton | 548/313 |
| 4,152,445 | 5/1979 | Wootton | 548/313 |

FOREIGN PATENT DOCUMENTS

2724948  12/1977  Fed. Rep. of Germany ............ 548/313

OTHER PUBLICATIONS

Smith et al., Jour. Med. Chem. 1977, vol. 20, No. 10, pp. 1292–1299.

*Primary Examiner*—Henry R. Jiles
*Assistant Examiner*—Jane T. Fan
*Attorney, Agent, or Firm*—Jacobs & Jacobs

[57] ABSTRACT

Compounds of the formula (I):

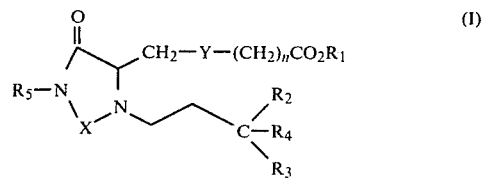

wherein:

Y is —$CH_2CH_2$—, —CH=CH— or —C≡C— n is 1 to 5;

$R_1$ is hydrogen, or $CO_2R_1$ represents an ester group in which the $R_1$ moiety contains from 1 to 12 carbon atoms;

$R_2$ is hydrogen, $C_{1-4}$ alkyl, trifluoromethyl, or phenyl;

$R_3$ is hydroxy or protected hydroxy;

$R_5$ is hydrogen, $C_{1-6}$ alkyl, phenyl or phenyl $C_{1-6}$ alkyl, any of which phenyl moieties may be substituted by one or more halogen, trifluoromethyl, $C_{1-6}$ alkyl, $C_{1-6}$ alkoxy or nitro groups; and X is $CH_2$ and $R_4$ is $C_{1-9}$ alkyl, $C_{3-8}$ cycloalkyl-$C_{1-6}$ alkyl, phenyl-$C_{1-6}$ alkyl or naphthyl-$C_{1-6}$ alkyl, any of which groups may have one acyclic carbon-carbon bond interrupted by an oxygen atom; hydrogen, $C_{3-8}$ cycloalky, phenyl or naphthyl, any of which phenyl of naphthyl moieties in $R_4$ may be substituted by one or more halogen, trifluoromethyl, $C_{1-6}$ alkyl, hydroxy, $C_{1-6}$ alkoxy or nitro groups; or $R_2$ and $R_4$ taken with the carbon atom to which they are joined represent a $C_{5-8}$ cycloalkyl group; or X is CS and $R_4$ is $C_{1-9}$ alkyl, $C_{3-8}$ cycloalkyl-$C_{1-6}$ alkyl, phenyl-$C_{1-6}$ alkyl or naphthyl-$C_{1-6}$ alkyl, having one acyclic carbon-carbon bond interrupted by an oxygen atom, and in which any phenyl or naphthyl moieties may be substituted by one or more halogen, trifluoromethyl, $C_{1-6}$ alkyl, hydroxy, $C_{1-6}$ alkoxy or nitro groups; and salts thereof; having similar pharmacological activity to natural prostaglandins, processes for their preparation, intermediates useful in those processes and pharmaceutical compositions containing compounds of the formula (I).

36 Claims, No Drawings

1,5-DISUBSTITUTED IMIDAZOLID-4-ONES

This invention relates to novel compounds having pharmacological activity, to a process for their preparation, to intermediates useful in that process and to pharmaceutical compositions containing them.

German Offenlegungsschrift No. 2724948 discloses that compounds of the general formula (A):

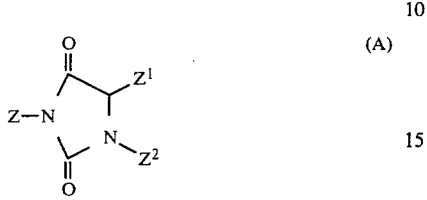

wherein Z is hydrogen or alkyl; one of $Z^1$ and $Z^2$ is a group $-CH_2-X-X^1-X^2$ in which X is phenylene, $-CH\equiv C-$, cis- or trans $-CH=CH-$ or $-CH_2-CO_2-$ where each radical Q independently of the other is hydrogen and/or alkyl or the two radicals Q together are $C_{4-6}$ alkylene, $X^1$ is a covalent bond or a straight or branched $C_{1-6}$ alkylene chain, in which one methylene group is optionally substituted by an oxa ($-O-$) group, with the proviso that at least one carbon atom separates the oxa group from a $-C\equiv C-$, $-CH=CH-$ or CO group, and $X^2$ is tetrazolyl, carboxyl, carboxamide, hydroxymethylene and/or alkoxycarbonyl; and the other one of $Z^1$ and $Z^2$ is a group $-Y-Y^1-Y^2-Y^3$ in which Y is $-CR_2-CH_2-$, where each radical R independently of the other is hydrogen and/or methyl, $Y^1$ is carbonyl, methylene, methylene substituted by a hydroxy group or methylene substituted by a hydroxy and alkyl group, $Y^2$ is a covalent bond or straight-chain or branched $C_{1-7}$ alkylene optionally substituted on the carbon atom adjacent to $Y^1$ by one or two mutually independent alkyl, bicycloalkyl or cycloalkyl groups, $Y^3$ is hydrogen, hydroxy, $C_{1-7}$ (preferably $C_{1-4}$) alkoxy, cycloalkyl, bicycloalkyl, phenyl, benzyl, phenoxy or benzyloxy, where each phenyl, benzyl, phenoxy or benzyloxy group may be substituted in the benzene ring by one or more hydroxy, halogen, nitro, amino, acylamino, alkenyl, alkoxy, phenyl and/or alkyl groups, which themselves may be substituted one or more halogens, or Y is a bond, $-CH_2-$ or $-CH_2.CH_2-$ and $Y^1$, $Y^2$ and $Y^3$ together are cycloalkyl which is substituted by a hydroxy group which is preferably separated by 3 carbon atoms from the hydantoin ring, have similar pharmacological activity to natural prostaglandins.

We have now discovered a class of compounds which have useful pharmacological activity and which are structurally distinct from the compounds disclosed in Offenlegungsschrift No. 2724948.

Accordingly, the present invention provides compounds of the formula (I):

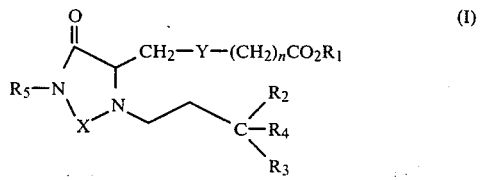

wherein:
Y is $-CH_2CH_2-$, $-CH=CH-$ or $-C\equiv C-$ n is 1 to 5;

$R_1$ is hydrogen, or $CO_2R_1$ represents an ester group in which the $R_1$ moiety contains from 1 to 12 carbon atoms;

$R_2$ is hydrogen, $C_{1-4}$ alkyl, trifluoromethyl, or phenyl;

$R_3$ is hydroxy or protected hydroxy;

$R_5$ is hydrogen, $C_{1-6}$ alkyl, phenyl or phenyl $C_{1-6}$ alkyl, any of which phenyl moieties may be substituted by one or more halogen, trifluoromethyl, $C_{1-6}$ alkyl, $C_{1-6}$ alkoxy or nitro groups; and X is $CH_2$ and $R_4$ is $C_{1-9}$ alkyl, $C_{3-8}$ cycloalkyl-$C_{1-6}$ alkyl, phenyl-$C_{1-6}$ alkyl or naphthyl-$C_{1-6}$ alkyl, any of which groups may have one acyclic carbon-carbon bond interrupted by an oxygen atom; hydrogen, $C_{3-8}$ cycloalkyl, phenyl or naphthyl, any of which phenyl or naphthyl moieties in $R_4$ may be substituted by one or more halogen, trifluoromethyl, $C_{1-6}$ alkyl, hydroxy, $C_{1-6}$ alkoxy or nitro groups; or $R_2$ and $R_4$ taken with the carbon atom to which they are joined represent a $C_{5-8}$ cycloalkyl group; or X is CS and $R_4$ is $C_{1-9}$ alkyl, $C_{3-8}$ cycloalkyl-$C_{1-6}$ alkyl, phenyl-$C_{1-6}$ alkyl or naphthyl-$C_{1-6}$ alkyl, having one acyclic carbon-carbon bond interrupted by an oxygen atom; and in which any phenyl or naphthyl moieties may be substituted by one or more halogen, trifluoromethyl, $C_{1-6}$ alkyl, hydroxy, $C_{1-6}$ alkoxy or nitro groups, and salts thereof.

Suitably Y is $-CH_2-CH_2-$.

Suitably n is 2, 3 or 4, preferably 3.

$R_1$ is hydrogen or $CO_2R_1$ represents an ester group in which the $R_1$ moiety contains from 1 to 12 carbon atoms. Examples of $R_1$ include hydrogen, methyl, ethyl, n- and iso- propyl, n-, sec- and tert-butyl, phenyl, benzyl, tolyl and the like, while normally hydrogen or $C_{1-6}$ alkyl groups are preferred.

Suitably $CO_2R_1$ can also represent an ester group which is readily hydrolysable in vivo to give the free acid. Examples of $R_1$ in this case include phthalidyl, pivaloyloxymethyl, 1-(ethoxycarbonyloxy)-ethyl and acetoxymethyl, more suitably phthalidyl.

Suitable examples of $R_2$ include hydrogen, methyl, ethyl and phenyl. More suitably $R_2$ is hydrogen, methyl, or ethyl, preferably methyl. $R_2$ may also be $CF_3$.

Suitable protected hydroxyl groups $R_3$ include readily hydrolysable groups such as acylated hydroxy groups in which the acyl moiety contains 1 to 4 carbon atoms, for example the acetoxy group; and hydroxyl groups esterified by readily removeable inert groups such as the benzyl group or like groups. Preferably $R_3$ is hydroxyl.

Suitable groups $R_4$ when $R_4$ is a $C_{1-9}$ alkyl group include $C_{4-9}$ alkyl groups. Such $C_{4-9}$ alkyl groups may be straight chain alkyl groups, such as n-pentyl, n-hexyl and n-heptyl, or may be alkyl groups branched by one or two methyl groups (at the same or different carbon atoms). Thus for example, $R_4$ may be a group $CH_2R_7$, $CH(CH_3)R_7$ or $C(CH_3)_2R_7$, wherein $R_7$ is a straight chain alkyl group such that the carbon content of the resultant group $R_4$ is 4 to 9.

In general preferred groups $R_4$ when $R_4$ is an alkyl group include straight chain pentyl, hexyl and heptyl groups. Of these, straight chain hexyl is often the most useful. Other preferred groups $R_4$ include groups CH(CH₃)R₇ and C(CH₃)₂R₇ wherein R₇ is straight chain butyl, pentyl and hexyl.

Other suitable examples of R₄ when R₄ is an alkyl group include the lower alkyl groups, that is when R₄ is a $C_{1-4}$ alkyl group.

When R₄ is or contains a $C_{3-8}$ cycloalkyl moiety, the moiety may for example be a cyclopropyl or cyclohexyl moiety. Examples of suitable $C_{1-6}$ alkyl moieties when R₄ is a $C_{3-8}$ cycloalkyl —$C_{1-6}$ alkyl group include methyl, ethyl, propyl, butyl and amyl.

When R₄ is an aryl group as preveiously defined, suitable groups R₄ include phenyl, phenylmethyl, phenylethyl, phenyl n-propyl, phenyl n-butyl, naphthyl, naphthyl-methyl, naphthyl-ethyl, naphthyl n-propyl and naphthyl n-butyl, and such groups branched in the alkyl moiety by one or two methyl groups (at the same or different carbon atoms). These groups may be substituted in the phenyl or naphthyl moiety by normally one, two or three groups selected from those substituent groups listed hereinbefore. Examples of suitable substituent groups include fluorine, chlorine and bromine atoms and CF₃, methyl, ethyl, n- and iso-propyl, methoxy and ethoxy, n- and iso-propoxy and nitro groups. Other examples of such groups include hydroxy. Preferably the aryl moieties when substituted by such groups will be mono or di-substituted.

When R₄ is a $C_{1-9}$ alkyl group interrupted by an oxygen atom, it may be represented as a $C_{1-8}$ alkoxy-$C_{1-8}$ alkyl group containing of course no more than 9 carbon atoms. Suitable examples of the alkyl moieties therein are as described above for a $C_{1-9}$ alkyl R₄ group.

More suitably, R₄ alkyl groups interrupted by an oxygen have the structure —CH₂—(CH₂)ⱼ—O—(CH₂)ₖ—CH₃, optionally substituted by one or two methyl groups at the same or different carbon atoms, wherein j and k are each 0 to 3 and j+k is 3 to 5 and preferably 4. Preferably k is 0 or 1, so that a specific example of such a group is —(CH₂)₅—O—Me.

When R₄ is $C_{3-8}$ cycloalkyl-$C_{1-6}$ alkyl, phenyl-$C_{1-6}$ alkyl or naphthyl-$C_{1-6}$ alkyl in which one acyclic carbon-carbon bond is interrupted by an oxygen atom, then it can suitably be a group of formula —CH₂—(CH₂)ₘ—O—(CH₂)ₓ —[cyclic moiety] optionally substituted by one or two methyl groups at the same or different acyclic carbon atoms, wherein m and x are 0 to 5 and m+x is no more than 5.

Also, R₂ and R₄ taken with the carbon atom to which they are joined can represent a $C_{5-8}$ cycloalkyl group, such as the cyclohexyl group.

Suitable examples of R₅ include hydrogen, methyl, ethyl, n- and iso-propyl, n-, sec- and tert-butyl; phenyl; phenylmethyl, phenethyl, phenyl-n-propyl, phenyl-n-butyl; and such phenylalkyl groups branched in their alkyl moieties by one or two methyl groups (at the same or different carbon atoms).

More suitably R₅ is $C_{1-6}$ alkyl such as methyl and ethyl, e.g. methyl.

When R₅ is or includes a phenyl moiety, it can optionally be substituted as described above for R₄ aryl groups.

The compounds of the formula (I) may form conventional salts. Such salts include those with alkali and alkaline earth metals, such as sodium and potassium, and ammonium and substituted ammonium salts.

The compounds of the formula (I) may also form conventional acid addition salts. Such salts include salts with pharmaceutically acceptable acids such as hydrochloric, hydrobromic, phosphoric, acetic, fumaric, salicylic, citric, lactic, mandelic, tartaric and methane-sulphonic acid.

A group of compounds within the compounds of the formula (I) as defined are those wherein X is CH₂ and R₄ is $C_{1-9}$ alkyl, $C_{3-8}$ cycloalkyl-$C_{1-6}$ alkyl, phenyl-$C_{1-6}$ alkyl or naphthyl-$C_{1-6}$ alkyl, any of which groups may have one acyclic carbon-carbon bond interrupted by an oxygen atom; hydrogen $C_{3-8}$ cycloalkyl, phenyl or naphthyl, any of which phenyl or naphthyl moieties in R₄ may be substituted by one or more halogen, trifluoromethyl, $C_{1-6}$ alkyl, hydroxy, $C_{1-6}$ alkoxy or nitro groups; or R₂ and R₄ taken with the carbon atom to which they are joined together a $C_{5-8}$ cycloalkyl group; and other variables are as defined in formula (I); and salts thereof.

From the aforesaid it will be seen that one particular suitable sub-group of compounds within formula (I) is of the formula (II):

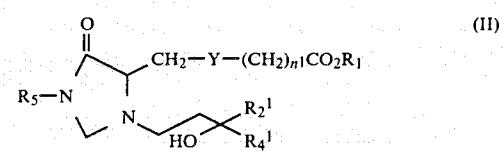

wherein:

Y, R₁ and R₅ are as defined in formula (I);

n¹ is 2, 3 or 4.

R₂¹ is hydrogen, methyl, ethyl or phenyl;

R₄¹ is hydrogen or $C_{1-9}$ alkyl; and salts thereof.

In formula (I) n¹ is preferably 3. Also Y is preferably —CH₂CH₂—.

R₂¹ is more suitably hydrogen, methyl or ethyl, preferably methyl.

While R₄¹ may be hydrogen or a $C_{1-9}$ alkyl group, it is normally a $C_{4-9}$ alkyl group. In such cases suitable and preferred straight chain and branched groups R₄¹ include those previously described as suitable and preferred for the group R₄ when R₄ is a $C_{4-9}$ alkyl group. Such preferred groups R₄¹ include straight chain pentyl, hexyl and heptyl, and of these normally the most useful is straight chain hexyl. Other preferred groups R₄¹ include CH(CH₃)R₇¹ and C(CH₃)₂R₇¹ wherein R₇¹ is straight chain butyl, pentyl or hexyl.

Suitably R₅ is $C_{1-6}$ alkyl such as methyl and ethyl, preferably methyl.

A second sub-group of compounds within formula (I) of particular interest are those of formula (III):

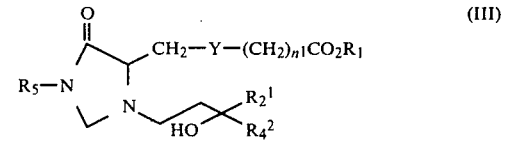

wherein:

Y, R₁ and R₅ are as defined in formula (I);

n¹ is 2, 3 or 4;

R₂¹ is hydrogen, methyl, ethyl or phenyl;

R₄² is a group of formula (IV):

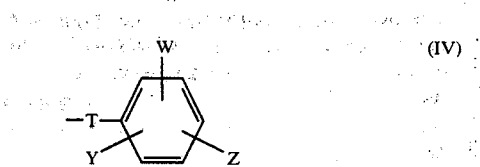

wherein T is a bond, or a $C_{1-6}$ alkylene group which may be straight chain or branched by one or two methyl groups at the same or different carbon atoms; and W, Y and Z are each hydrogen or fluorine, chlorine or bromine atoms, or $CF_3$, methyl, ethyl, n- or iso-propyl, methoxy, ethoxy, n- or iso-propoxy or nitro groups; and salts thereof.

In formula (III) $n^1$ is preferably 3. Also Y is preferably $-CH_2CH_2-$;

$R_2^1$ is more suitably hydrogen, methyl or ethyl, preferably methyl.

In formula (IV) often T will be a group $-(CH_2)_q-$ wherein q is 0 to 4. Also, suitably W and Y are hydrogen.

Suitably $R_5$ is $C_{1-6}$ alkyl such as methyl and ethyl, preferably methyl.

A further sub-group of compounds within formula (I) of interest is of formula (V):

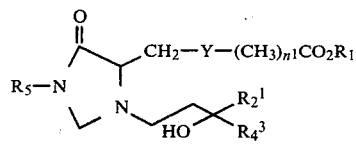

wherein:
Y, $R_1$ and $R_5$ are as defined in formula (I):
$n^1$ is 2, 3 or 4;
$R_2^1$ is hydrogen, methyl, ethyl or phenyl;
$R_4^3$ is a group of formula (VI):

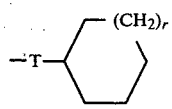

wherein
T is as defined in formula (IV) and r is 0 to 3; and salts thereof.

In formula (V) $n^1$ is preferably 3. Also Y is preferably $-CH_2CH_2-$;

$R_2^1$ is more suitably hydrogen, methyl or ethyl, preferably methyl.

In formula (VI) often T will be a group $-(CH_2)_q-$ wherein q is 0 to 4. Also suitably r is 1.

Suitably $R_5$ is $C_{1-6}$ alkyl such as methyl and ethyl, preferably methyl.

A further sub-group of compounds within formula (I) of interest is of formula (II) as defined, but wherein $R_4^1$ is a $C_{1-9}$ alkyl, $C_{3-8}$ cycloalkyl-$C_{1-6}$ alkyl or phenyl-$C_{1-6}$ alkyl group in which groups one acyclic carbon-carbon bond is interrupted by an oxygen atom and in which any phenyl moiety may be optionally substituted as hereinbefore described.

In this sub-group preferred $R_4$ groups include an alkyl group interrupted by oxygen which may be represented as a $C_{1-8}$ alkoxy-$C_{1-8}$ alkyl group containing of course no more than 9 carbon atoms, as hereinbefore described.

Another sub-group of compounds within formula (I) is of formula (VII):

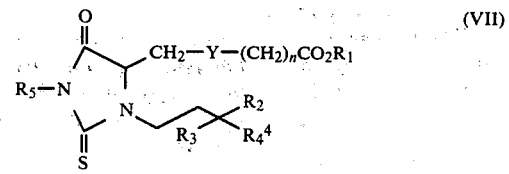

wherein:
$R_4^4$ is $C_{1-9}$ alkyl, $C_{3-8}$ cycloalkyl-$C_{1-6}$ alkyl, phenyl-$C_{1-6}$ alkyl or naphthyl-$C_{1-6}$ alkyl, having one acyclic carbon-carbon bond interrupted by an oxygen atom; in which phenyl or napthyl moieties may be substituted by one or more halogen, trifluoromethyl, $C_{1-6}$ alkyl, hydroxy, $C_{1-6}$ alkoxy or nitro groups; and the remaining variables are as defined in formula (I).

Suitable and preferred variables other than $R_4^4$ are as so described below formula (I).

Suitable and preferred $R_4^4$ are as so described under formula (I) for $R_4$ having one acyclic carbon-carbon bond interrupted by an oxygen atom.

In the sub-groups hereinbefore described, $R_1$ is hydrogen or $CO_2R_1$ represents as ester group, in which the $R_1$ moiety contains from 1 to 12 carbon atoms.

Preferably in the sub-groups $R_1$ is hydrogen, or a $C_{1-6}$ alkyl group.

However it is believed that in the sub-groups, compounds where $CO_2R_1$ is an in vivo hydrolysable ester will also be of particular interest as ready sources of the corresponding free acid. Examples of $R_1$ in each case include phthalidyl, pivaloyloxymethyl, 1-(ethoxycarbonyloxy)ethyl and acetoxymethyl, more suitably phthalidyl.

It will of course be realised that the compounds of the formula (I) have asymetric centres, and thus are capable of existing in a number of stereoisomeric forms. The invention extends of each of these stereoisomeric forms, and to mixtures thereof. The different steroisomeric forms may be separated one from the other by the usual methods.

The present invention further provides a process for the preparation of the compounds of the formula (I), wherein X is $CH_2$, which process comprises reducing a compound of the formula (IX):

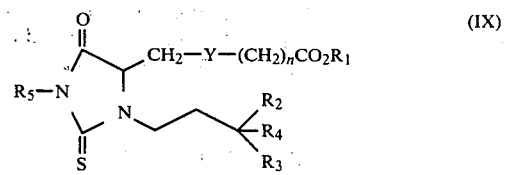

wherein $R_4^5$ is as defined for $R_4$ when $X=CH_2$ is formula (I) and remaining groups are as hereinbefore defined; and thereafter if desired or necessary converting Y, $R_1$, $R_3$ or a $R_5$ hydrogen in the compound thus formed into another Y, $R_1$, $R_3$ or $R_5$.

The reductive desulphurisation may be carried out in the presence of a suitably conventional hydrogenation catalyst, such as Raney nickel, under conventional conditions for such reactions. For example a solution of the chosen compound of the formula (IX) in an organic solvent may be added to a refluxing suspension of the catalyst in a similar solvent. It will be appreciated by the skilled man that when Y is —CH=CH— or —C≡C—, the reaction conditions must be selected having regard to the reactivity of Y.

The present invention also provides a process for the preparation of the compounds of the formula (I) wherein X is CS, i.e. the compounds of the formula (VII), which process comprises the cyclisation of a compound of the formula (VIII):

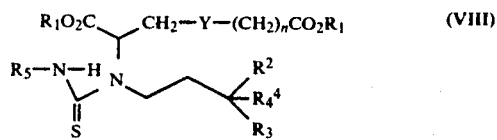

wherein the variable groups are as hereinbefore defined.

Preparation of Intermediates

The same process may be used for the preparation of the intermediates of the formula (IX) by the cyclisation of a compound of formula (X):

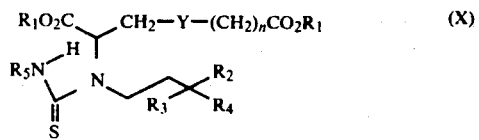

wherein the variable groups are as hereinbefore defined in formula (IX).

Either cyclisation may suitably be carried out by warming the compound of the formula (VIII) or (X) alone, or by heating the compound of the formula (VIII) or (X) in an inert organic solvent such as benzene or the like, suitably under reflux. When $R_5$ is hydrogen the solvent should be non-hydroxylic. In some cases the necessary cyclisation of the compound of the formula (VIII) or (X) under these conditions can only be achieved in the presence of a strong base, such as sodium hydride or sodium ethoxide, in a dry organic solvent. This may be necessary when $R_5$ is a sterically hindered group.

When $R_5$ is hydrogen, such compounds of the formula (VIII) or (X) can be prepared by reacting a salt $M^+ CNS^-$, wherein $M^+$ is a metal ion, with a compound of the formula (XI) or (XII) respectively in the presence of an acid, e.g. by using a mineral acid such as aqueous hydrochloride acid, or a corresponding acid addition salt of the compound of the formula (XI) or (XII) respectively:

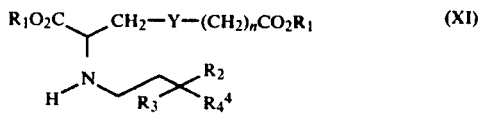

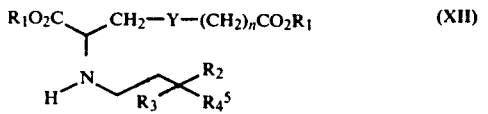

wherein the variable groups are as hereinbefore defined. This reaction can conveniently be carried out at room temperature. Suitably $M^+$ is a sodium or potassium ion.

When both $R_1$ and $R_5$ are other than hydrogen in the compound of the formula (VIII) or (X), the compound of the formula (VIII) or (X) is conveniently prepared by the reaction of a compound of the formula (XI) or (XII) respectively with $R_5NCS$ wherein $R_5$ is not hydrogen in an inert organic solvent such as benzene or the like, a preferred process of the invention.

In this case the compound of the formula (VIII) or (X) is conveniently cyclised in situ, suitably under reflux in the organic solvent used. The presence of a strong base may be necessary as noted above.

Intermediates of the formulae (VIII) and (XI) are believed to be novel and form an aspect of the present invention.

The conversion of a compound of the formula (I), wherein Y, $R_1$, $R_3$ or $R_5$ (when $R_5$ is hydrogen) is altered when desired or necessary, may be achieved in a conventional manner. The conversion of a compound of formula (I) wherein X=CS, i.e. a compound of formula (VIII), to a compound wherein X=CH$_2$, may be achieved in the manner hereinbefore described for the conversion of a compound of the formula (IX) to a compound of the formula (I) wherein X=CH$_2$.

By way of example of such conversions the group $R_1$ in the compound of the formula (I) may be varied by conventional esterification and/or de-esterification.

Similary, it will be realised that when a compound is desired wherein $CO_2R_1$ is an ester group which is readily hydrolysable in vivo to the free acid it may be preferred to convert the group $CO_2R_1$ to such an ester group as a final reaction step.

Similarly, if desired compounds wherein Y is —C≡C— may be reduced to compounds wherein Y is —CH=CH— in known manner. Suitably this reaction is carried out using catalytic hydrogenation, such as Lindlar catalysis.

When Y is —CH=CH—, it may be reduced to —CH$_2$—CH$_2$— in known manner, suitably using catalytic hydrogenation such as transistion-metal catalysis.

Protected $R_3$ hydroxyl moieties may be deprotected in conventional manner. For example when $R_3$ is a benzyloxy group, the benzyl group may be removed by hydrogenolysis. Thus it may be seen that 'protected hydroxy' compounds of the formula (I) are useful intermediates in the preparation of the corresponding 'free hydroxy' compounds of the formula (I).

Also, when $R_5$ is hydrogen, compounds of the formula (I) may be converted to corresponding compounds but with different $R_5$ values by conventional substitution reactions with $R_5X$ wherein X is a displaceable group such as a halide or other good leaving group. In such reactions it may be necessary to first convert the compound of the formula (I) to an alkali metal salt of the $R_5$ hydrogen.

The skilled man will realise that in some cases substituting a $R_5$ hydrogen will also substitute a $R_1$ hydrogen. Thus if a compound is desired wherein $R_1$ is hydrogen and $R_5$ is substituted, in such cases it will be preferred to esterify the $R_1$ hydrogen before the substitution reaction, and then de-esterify after the substitution reaction, to give the desired $R_1$ hydrogen compound.

When a compound of the formula (I) contains an acidic hydrogen atom, salts thereof may be prepared in a conventional manner by for example reacting the compound of the formula (I) with the required base. For salts of compounds wherein $R_5$ is hydrogen, the base should be a strong base such as for example sodium in an alcohol such as ethanol, or the like.

Compounds of the formula (I) contain a basic nitrogen atom when X is $CH_2$, and acid addition salts thereof may be prepared in a conventional manner by for for example reacting the compound of the formula (I) with the required acid.

Compounds of formula (XI) or (XII) may conveniently be prepared by a process which comprises reacting a compound of formula (XIII): $R_1O_2C-CH(Q_1)-CH_2-Y-(CH_2)_nCO_2R_1$ with a compound of the formula (XIV): $Q_2(CH_2)_2CR_2R_3R_4^5$ or (XV): $Q_2(CH_2)_2CR_2R_3R_4^4$ in which compounds one of $Q_1$ and $Q_2$ is amino and the other of $Q_1$ and $Q_2$ is a good leaving group, such as tosylate or a halide or like readily displaceable group. Preferred examples of such good leaving groups include bromide.

This displacement reaction is suitably carried out in an inert organic solvent, such as hexamethylphosphoramide or N,N-dimethylformamide, at non-extreme temperature, in the presence of a base, such as sodium carbonate or sodium hydride, and a source of alkali metal ions, such as an alkali metal halide. Suitable alkali halides include sodium iodide and lithium iodide.

Preparative procedures of this general nature for the synthesis of compounds of the formula (XI) or (XII) are described in Offenlegungsschriften Nos: 2552312, 2647969 and 2724948.

Compounds within the formula (I) have useful pharmacological activity. For example compounds within the formula (I) have anti-gastric secretion activity e.g. anti-ulcer activity, cardiovascular activity, platelet aggregation inhibition activity, affect the respiratory tract e.g. bronchodilator activity, and have anti-fertility, smooth muscle and anti-arrhythmic activity.

In general it may be said that compounds within the formula (I) have a range of pharmacological activities similar to those shown by the natural prostaglandins, but that these activities tend to be rather more selective. The compounds of the formula (I) have particularly useful bronchodilator activity.

The invention therefore also provides a pharmaceutical composition comprising a compound of the formula (I) and a pharmaceutically acceptable carrier.

Clearly the formulation of the said pharmaceutical composition will depend on the nature of the activity shown by the chosen compound of the formula (I), and on other factors such as a preference in a particular area of therapy for a particular mode of administration.

The compositions may be in the form of tablets, capsules, powders, granules, lozenges or liquid preparations, such as oral or sterile parenteral solutions of suspensions.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oil suspensions, solutions, emulsions, syrups, or elixirs, or may be presented as a dry product for reconstitution with water or other suitable vehicle before use. Such liquid preparations may contain conventional additives such as suspending agents, emulsifying agents, non-aqueous vehicles (which may include edible oils), preservatives, and if desired conventional flavouring or colouring agents, and the like.

For parenteral administration, fluid unit dosage forms are prepared utilizing the compounds of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

When appropriate, the compositions of this invention may be presented as an aerosol for oral administration, or as a microfine powder for insufflation.

As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention also provides a method of treatment and/or propylaxis of disorders in human beings and animals which comprises the administration to the sufferer of an effective amount of a compound of the formula (I).

The following Examples 2 and 3 illustrate the preparation of compounds of the formula (I) and their pharmacological properties.

EXAMPLE 1

Compound 1

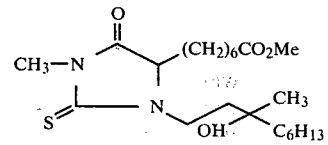

Dimethyl 2-[N-3'-hydroxy-3'-methyl-n-nonyl-]aminoazelate (10 g) was refluxed with methyl isothiocyanate (1.89 g) in try toluene (100 ml) for 3 hours. The toluene was evaporated in vacuo to give a yellow oil (11.1 g). The oil was chromatographed on kieselgel (330 g) using chloroform as eluant to give 1-(3'-hydroxy-3'-methyl-n-nonyl)-3-methyl-5-(6''-methoxycarbonyl-n-hexyl)-2-thiohydantoin (9.49 g) as a pale yellow oil.

The compounds shown in Table 1 were prepared in similar manner:

TABLE 1

| Compound number | $R_1$ | $R_2$ | $R_4$ | $R_5$ | d |
|---|---|---|---|---|---|
| 2 | $CH_3$ | $CH_3$ | Ph | $CH_3$ | 6 |
| 3 | $CH_3$ | $CH_3$ | $CH(CH_3)C_4H_9$ | $CH_3$ | 6 |

TABLE 1-continued

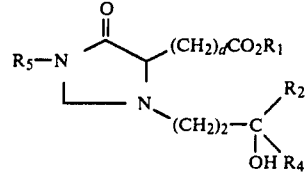

| Compound number | $R_1$ | $R_2$ | $R_4$ | $R_5$ | d |
|---|---|---|---|---|---|
| 4 | $CH_3$ | | | $CH_3$ | 6 |
| 5 | $CH_3$ | $CH_3$ | $C_2H_5$ | $CH_3$ | 6 |
| 11 | $CH_3$ | $CH_3$ | $CH_3$ | $CH_3$ | 6 |
| 12 | $CH_3$ | H | $C_2H_5$ | $CH_3$ | 6 |
| 13 | $CH_3$ | $CH_3$ | | $CH_3$ | 6 |
| 14 | $CH_3$ | $CH_3$ | $C_5H_{11}$ | $CH_3$ | 6 |

EXAMPLE 2

Compound 6

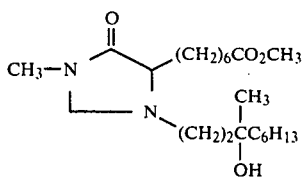

1-(3'-hydroxy-3'-methyl-n-nonyl)-3-methyl-5-(6''-methoxy-carbonyl-n-hexyl)-2-thiohydantoin (3.3 g) in methanol (10 ml) was added, over five minutes, to a stirred, refluxing, suspension of Raney nickel [NICAT 101]* (c. 20 g) in methanol (100 ml); reflux was continued for thirty minutes. The hot suspension was filtered through kieselguhr and the residue was well washed with methanol. The methanol solution was evaporated in vacuo and the residue was dissolved in ether.

*Raney nickel [NICAT 101] was supplied by Joseph Crosfield and Sons Limited, P.O. Box 26, Warrington, WA5 1AB, Cheshire.

The ether solution was washed with water and dried and evaporated in vacuo to give a yellow gum (2.4 g) which was purified via column chromatography on silica gel using chloroform/1% methanol as eluant to give 1-(3'-hydroxy-3'-methyl-n-nonyl)-3-methyl-5-(6''-methoxycarbonyl-n-hexyl)-4-imidazolidone (2.3 g) as a clear gum.

The compounds shown in Table 2 were produced in a similar manner.

TABLE 2

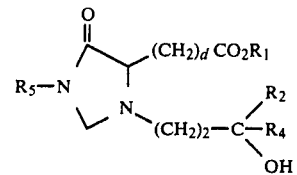

| Compound Number | $R_1$ | $R_2$ | $R_4$ | $R_5$ | d |
|---|---|---|---|---|---|
| 7 | $CH_3$ | $CH_3$ | Ph | $CH_3$ | 6 |
| 8 | $CH_3$ | $CH_3$ | $CH(CH_3)C_4H_9$ | $CH_3$ | 6 |
| 9 | $CH_3$ | | | $CH_3$ | 6 |
| 10 | $CH_3$ | $CH_3$ | $C_2H_5$ | $CH_3$ | 6 |
| 15 | $CH_3$ | H | $C_2H_5$ | $CH_3$ | 6 |

TABLE 2-continued

| Compound Number | $R_1$ | $R_2$ | $R_4$ | $R_5$ | d |
|---|---|---|---|---|---|
| 16 | $CH_3$ | $CH_3$ | $C_5H_{11}$ | $CH_3$ | 6 |

EXAMPLE 3

The compounds shown in Table 3 may be prepared in similar manner to the compounds listed in Table 2 of Example 2, from the corresponding intermediate compounds 11 and 13.

TABLE 3

| Compound Number | $R_1$ | $R_2$ | $R_4$ | $R_5$ | d |
|---|---|---|---|---|---|
| 17 | $CH_3$ | $CH_3$ | $CH_3$ | $CH_3$ | 6 |
| 18 | $CH_3$ | $CH_3$ | | $CH_3$ | 6 |

CHARACTERISING DATA

Compound 1 (The compound of Example 1)

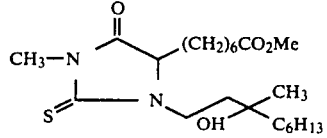

I.R. (cm$^{-1}$): 3510, [OH];

1750 to 1720 [—N—C—N—C—; $CO_2CH_3$]
                    ‖    ‖
                    S    O

NMR (τ): 7.75, (m), [OH; $CH_2$—$CO_2CH_3$];
6.8, (s), [—N—$CH_3$];
7 to 6.2, (m), [—N—$CH_2$];
6.35, (s), [—$CO_2CH_3$];
5.9, (m), [—N—CH].

Analysis: $C_{22}H_{40}N_2O_4S$
requires: C, 61.64; H, 9.41; N, 6.53; S, 7.48%
found: C, 61.71; H, 9.51; N, 6.54; S, 7.34%
Mass Spec.: $C_{22}H_{38}N_2O_3S$ [m*-$H_2O$]
requires: 410.2603
found: 410.2610

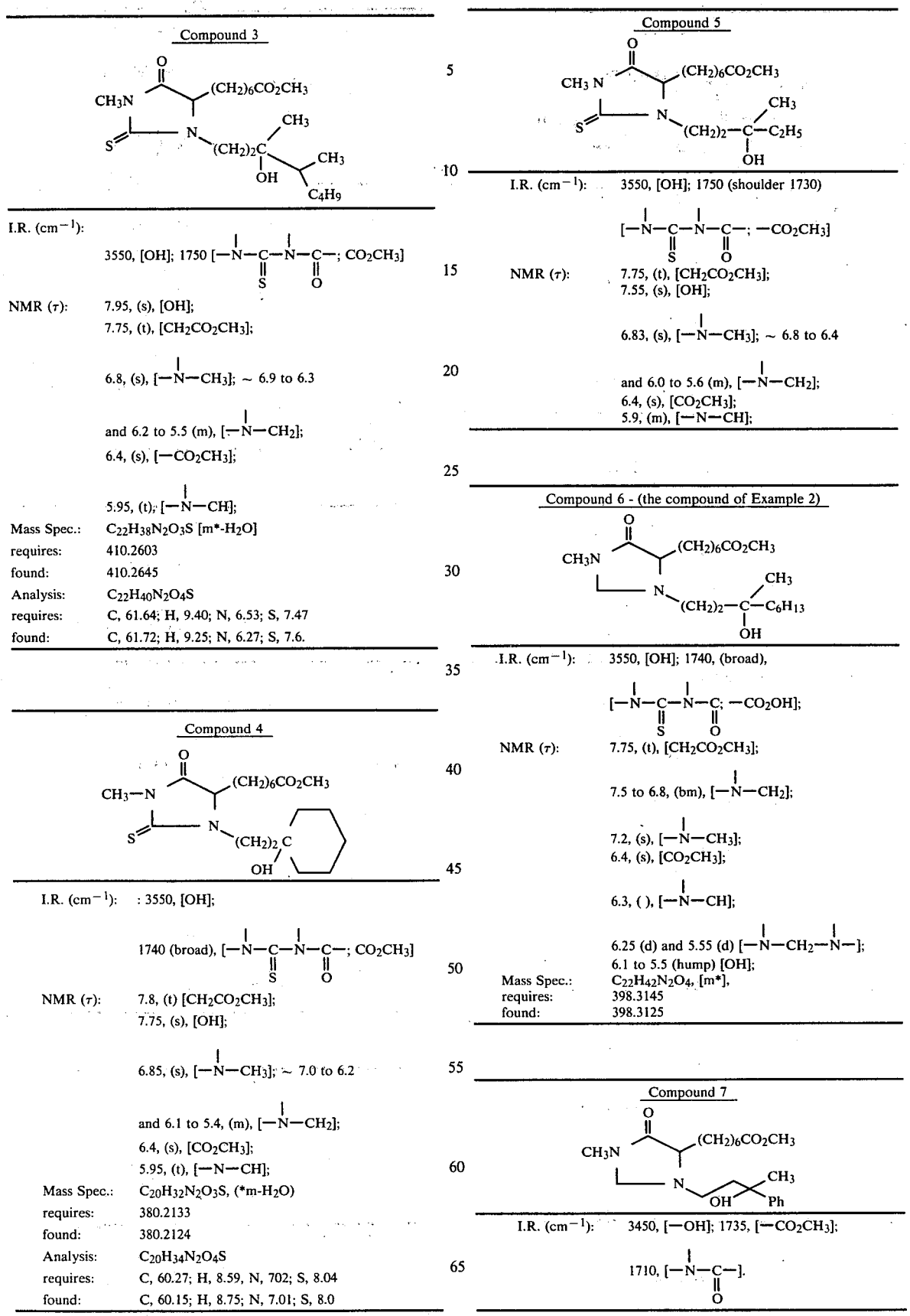

-continued

Compound 8

Structure: CH$_3$NH-C(=O)-CH((CH$_2$)$_6$CO$_2$CH$_3$)-N(CH$_2$-)-(CH$_2$)$_2$-C(OH)(CH$_3$)-CH(CH$_3$)-C$_4$H$_9$ I.R. (cm$^{-1}$): 3500 [OH]; 1740, [CO$_2$CH$_3$]; 1710, [CH$_3$N–];

NMR (τ):
- 7.75, (t), [CH$_2$CO$_2$CH$_3$];
- 7.5 to 6.8, (m), [—N—CH$_2$];
- 7.2, (s), [—N—CH$_3$];
- 6.4, (s), [—CO$_2$CH$_3$];
- 6.3, [—N—CH];
- 6.25 (d) and 5.55 (d), [—N—CH$_2$—N—]
- 6.1 to 5.1, (hump), [OH];

Compound 9

Structure: CH$_3$NH-C(=O)-CH((CH$_2$)$_6$CO$_2$CH$_3$)-N(CH$_2$-)-(CH$_2$)$_2$-C(OH)(cyclohexyl)

I.R. (cm$^{-1}$): 3500, [OH]; 1740, [CO$_2$CH$_3$]; 1710, [CH$_3$—N—C(=O)—]

NMR (τ):
- 7.65, (t), [CH$_2$CO$_2$CH$_3$];
- 7.1, (s), [—N—CH$_3$];
- 7.4 to 6.5, (bm), [—N—CH$_2$];
- 6.3, (s), [CO$_2$CH$_3$];
- 6.2, (m), [—N—CH];
- 6.15 (d) and 5.45 (d), [—N—CH$_2$—N—];
- 6.1 to 5.6, (hump), [OH];

Compound 10

Structure: CH$_3$NH-C(=O)-CH((CH$_2$)$_6$CO$_2$CH$_3$)-N(CH$_2$-)-(CH$_2$)$_2$-C(OH)(CH$_3$)-C$_2$H$_5$ IR (cm$^{-1}$): 3450, [—OH]; 1740, [—CO$_2$CH$_3$]; 1710, [—N—C(=O)—]

N.M.R. (τ): 
- 7.75, (t), [—CH$_2$CO$_2$CH$_3$];

Compound 10

Structure: CH$_3$NH-C(=O)-CH((CH$_2$)$_6$CO$_2$CH$_3$)-N(CH$_2$-)-(CH$_2$)$_2$-C(OH)(CH$_3$)-C$_2$H$_5$

- 7.2 (brm), [—N—CH$_2$—];
- 7.2, (s), [—N—CH$_3$];
- 6.4, (s), [—CO$_2$CH$_3$];
- 6.3, (brm), [—N—CH<];
- 6.25 and 5.6, (pd) [—N—CH$_2$—N—].

Mass. Spec.: C$_{18}$H$_{34}$N$_2$O$_4$ [m*]
requires: 342.2519
found: 342.2555

Compound 11

Structure: CH$_3$—N(–C(=O)–)–CH((CH$_2$)$_6$CO$_2$Me)–N(–C(=S)–)–CH$_2$–C(CH$_3$)$_2$–OH (cyclic diketone/thione ring)

I.R. (cm$^{-1}$): 3500, [OH]; 1740, 1720, [—N—C(=S)—N—C(=O)—; —CO$_2$CH$_3$]

NMR (τ):
- 7.75, (brm), [—CH$_2$CO$_2$CH$_3$];
- 7.45, (s), [OH];
- 6.8, (s), [—N—CH$_3$];
- 6.5, (brm), [—N—CH$_2$—];
- 6.4, (s), [—CO$_2$CH$_3$];
- 5.9, (m), [—N—CH<];

Mass Spec.: C$_{17}$H$_{30}$N$_2$O$_4$S [m*]
requires: 358.1926
found: 358.1956

Compound 12

Structure: CH$_3$—N(–C(=O)–)–CH((CH$_2$)$_6$CO$_2$Me)–N(–C(=S)–)–CH$_2$–CH(OH)–C$_2$H$_5$ I.R. (cm$^{-1}$): 3500, [OH]; 1740 (broad) [—N—C(=S)—N—C(=O)—; —CO$_2$CH$_3$].

NMR (τ): 7.7, (t), (—CH$_2$CO$_2$CH$_3$];

-continued

Compound 12

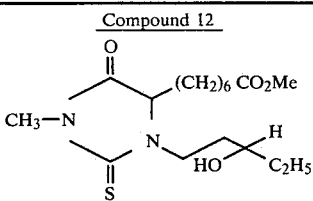

|  |  |
|---|---|
| | 6.75, (s), [−N−CH₃]; |
| | 6.5, (brm), [−N−CH₂−]; |
| | 6.4, (s), [−CO₂CH₃]; |
| | 5.85, (m), [−N−CH<]. |
| Analysis: requires: | $C_{17}H_{30}N_2O_4S$ C, 56.96; H, 8.43; N, 7.81; S, 8.94%. |
| found: | C, 57.07; H, 8.67; N, 7.66; S, 8.53%. |
| Mass Spec. requires found | $C_{17}H_{30}N_2O_4S$ [M*]. 358.1926. 358.1894. |

COMPOUND 13

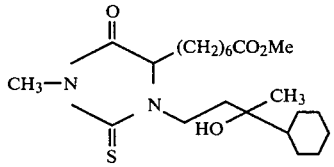

| I.R (cm⁻¹): | 3470, [OH]; 1740 (broad), [−N−C−N−C−; −CO₂CH₃] ‖ ‖ S O |
|---|---|
| NMR (τ): | 7.8, (t), [−CH₂CO₂CH₃]; 7.75, (bs), [OH]; |
| | 6.7, (brm), [−N−CH₂]; |
| | 6.8, (s), [−N−CH₃]; 6.4, (s), [−CO₂CH₃]; |
| | 5.9, (m), [−N−CH<]. |
| Mass Spec: requires: found: | $C_{22}H_{36}N_2O_3S$ [M*−H₂O]; 408.2430 408.2437 |

COMPOUND 14

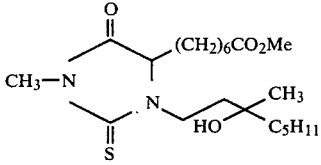

| I.R (cm⁻¹): | 3470, [OH]; 1740 (broad), [−N−C−N−C−; CO₂CH₃] ‖ ‖ S O |
|---|---|

COMPOUND 14

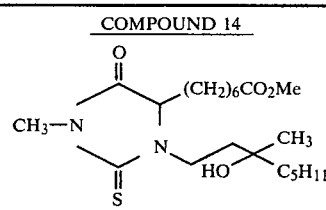

| NMR (τ): | 7.85, (t), [−CH₂CO₂CH₃]; 7.75, (s), [OH]; |
|---|---|
| | 6.6, (brm), [−N−CH₂−]; |
| | 6.8, (s), [−N−CH₃]; 6.4, (s), [−CO₂CH₃]; |
| | 5.9, (m), [−N−CH<]. |
| Analysis: requires: | $C_{21}H_{38}N_2O_4S$ C, 60.85; H, 9.24; N, 6.76; S, 7.73%. |
| found: | C, 60.51; H, 9.31; N, 6.35; S, 7.92%. |
| Mass Spec.: requires: found: | $C_{21}H_{38}N_2O_4S$ [M*]; 414.2581 414.2565 |

COMPOUND 15

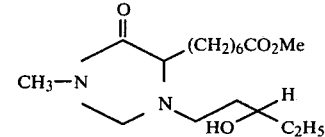

| I. R (cm⁻¹): | 3450, [−OH]; 1740 [−CO₂CH₃]; |
|---|---|
| | 1710, [−N−C−]. ‖ O |
| NMR (τ): | 7.75, (t), [−CH₂CO₂CH₃]; |
| | 7.2, (brm), [−N−CH₂−]; |
| | 7.15, (s), [−N−CH₃]; |
| | 6.3, (brm) [−N−CH<; >CHOH]; |
| | 6.3, (s), [−CO₂CH₃]; |
| | 6.2 and 5.55, (dd), [−N−CH₂−N−]. |
| Mass Spec.: requires: found: | $C_{17}H_{32}N_2O_4$ [M*]. 328.2362 328.2354. |

COMPOUND 16

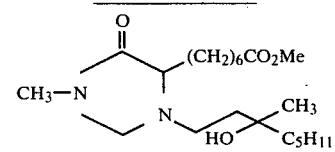

| I. R (cm⁻¹): | 3430, [OH]; 1735, [−CO₂CH₃]; |
|---|---|

-continued

COMPOUND 16

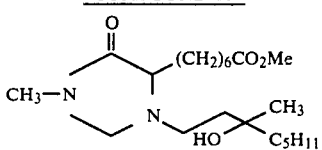

NMR (τ): 1700, [—N—C—];
    ‖
    O 7.75, (t), [—CH$_2$CO$_2$CH$_3$];

7.2, (brm), [—N—CH$_2$—];

7.15, (s), [—N—CH$_3$];

6.3, (brm), [—N—CH< ; OH];

6.2 and 5.55 (dd), [—N—CH$_2$—N—].

PHARMACOLOGICAL DATA

1. Bronchodilation Activity

The compounds were examined for their ability to inhibit 5-hydroxytryptamine or histamine induced bronchoconstristion in the anaesthetised, artifically respired guinea pig (Konzett-Rossler preparation). The compounds were administered intravenously. The results are shown in the Table.

| Compound Number | ID50 against 5-hydroxytryptamine induced constriction g/Kg, i.v. |
| --- | --- |
| 6 | 30 |

2. Anti-ulcer activity

Method

Anti-ulcer activity was assessed by the inhibition of indomethacin induced gastric damage in the rat according to the method of Eleghe (1974) Israeli J. Med. Sci. 10. 1451. Rats were starved overnight and given 15 mg/kg indomethacin subcutaneously and sacrificed 4 hours later. Stomachs were reflated with n. saline, cut along the greater curvature pinned out and scored for gastric damage by the following system:

Score 1–3—according to degree of erythema and slight haemorrhage.
Score 4–6—according to degree of muscosal erosion.
Score 7–9—according to depth of gastric damage.

Groups of 7 rats were used for each treatment and the test compound or vehicle were administered 30 minutes prior to giving the indomethacin. Dose of test compound was 100 mg/kg orally and control groups receiving vehicle only were obtained using the above scoring system and the Mann Witney test applied for significance of difference between the values obtained with the treatments.

The results are shown in the Table:

| Compound Number | Vehicle Control Mean Score ± S.E. of Mean | Test Compound Mean Score ± S.E. of Mean |
| --- | --- | --- |
| 6 | 3.71 ± 0.80 | 0.71 ± 0.42 (P<0.01) |

3. Toxcity

No toxic effects were observed at the test dosage.

I claim:

1. A compound of the formula:

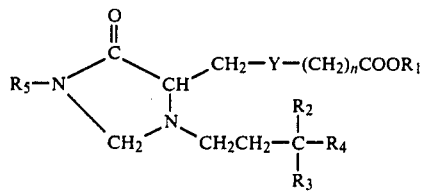

the pharmaceutically acceptable acid addition salt thereof, and the alkali metal, alkaline earth metal, ammonium and substituted ammonium salt when $R^1$ is hydrogen wherein Y is —CH$_2$CH$_2$—, —CH=CH— or —C≡C—;
n is 1 to 5;
R$_1$ is hydrogen, alkyl of 1 to 12 carbon atoms, phenyl, benzyl, tolyl, phthalidyl, pivaloyloxymethyl, 1-ethoxy-carbonyloxyethyl or acetoxymethyl;
R$_2$ is hydrogen, alkyl of 1 to 4 carbon atoms, trifluoromethyl or phenyl;
R$_3$ is hydroxy, alkanoyoxy of 1 to 4 carbon atoms or benzyloxy;
R$_5$ is hydrogen, alkyl of 1 to 6 carbon atoms, phenyl or phenylalkyl wherein alkyl has 1 to 6 carbon atoms, said phenyl and phenylalkyl being unsubstituted or substituted with one or more members selected from the group consisting of halo, trifluoromethyl, alkyl of 1 to 6 carbon atoms, alkoxy of 1 to 6 carbon atoms, and nitro; and
R$_4$, when taken alone, is (a) hydrogen; (b) unsubstituted alkyl of up to 9 carbon atoms; (c) alkoxyalkyl of up to 9 carbon atoms; (d) cycloalkyl of 3 to 8 carbon atoms; (e) phenyl; (f) naphthyl; (g) alkyl of up to 6 carbon atoms substituted with cycloalkyl of 3 to 8 carbon atoms; (h) alkyl of up to 6 carbon atoms substituted with phenyl; (i) alkyl of up to 6 carbon atoms substituted with naphthyl; (j) —CH$_2$(CH$_2$)$_m$—O—(CH$_2$)$_x$-cycloalkyl wherein each m and x have a value of from 0 to 5 with the sum of m+x being no more than 5 and cycloalkyl contains from 3 to 8 carbon atoms; (k)—CH$_2$(CH$_2$)$_m$—O—(CH$_2$)$_x$-phenyl wherein m and x are as herein defined; or (l) —CH$_2$(CH$_2$)$_m$—O—(CH$_2$)$_x$-naphthyl wherein m and x are as herein defined; any of said phenyl or naphthyl being unsubstituted or substituted by one or more members selected from the group consisting of halo, trifluoromethyl, alkyl of 1 to 6 carbon atoms, hydroxy, alkoxy of 1 to 6 carbon atoms and nitro; or
R$_4$, when taken with R$_2$, is alkylene of 4 to 7 carbon atoms .

2. A compound according to claim 1 and having the formula:

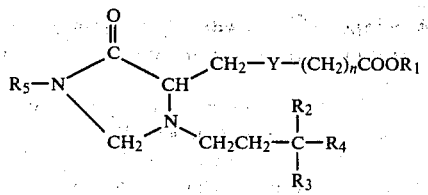

the pharmaceutically acceptable acid addition salt thereof, and the alkali metal, alkaline earth metal, ammonium and substituted ammonium salt when $R^1$ is hydrogen
wherein
  Y, $R_1$ and $R_5$ are as therein defined;
  n is 2, 3 or 4;
  $R_2$ is hydrogen, methyl, ethyl or phenyl; and
  $R_4$ is hydrogen or alkyl of 1 to 9 carbon atoms.

3. A compound according to claim 1 and having the formula:

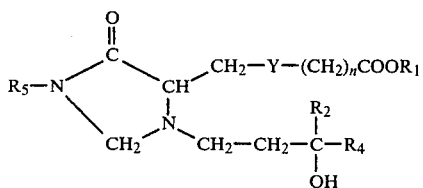

the pharmaceutically acceptable acid addition salt thereof, and the alkali metal, alkaline earth metal, ammonium and substituted ammonium salt when $R^1$ is hydrogen
wherein
  Y, $R_1$ and $R_5$ are as therein defined;
  n is 2, 3 or 4;
  $R_2$ is hydrogen, methyl, ethyl or phenyl; and
  $R_4$ is (a) unsubstituted alkyl or alkoxyalkyl of up to 9 carbon atoms; (b) alkyl or alkoxyalkyl of up to 6 carbon atoms substituted by cycloalkyl of 3 to 8 carbon atoms or phenyl, said phenyl being unsubstituted or substituted with one or more members selected from the group consisting of halo, trifluoromethyl, alkyl of 1 to 6 carbon atoms, hydroxy, alkoxy of 1 to 6 carbon atoms and nitro.

4. A compound according to claim 1 and having the formula:

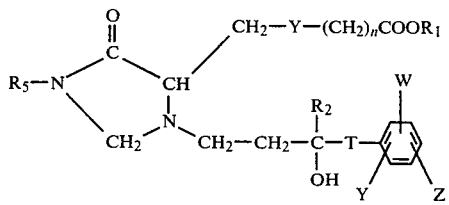

the pharmaceutically acceptable acid addition salt thereof, and the alkaline metal, alkaline earth metal, ammonium and substituted ammonium salt when $R^1$ is hydrogen
wherein
  Y, $R_1$ and $R_5$ are as therein defined;
  n is 2, 3 or 4;
  $R_2$ is hydrogen, methyl, ethyl or phenyl;
  T is carbon-carbon bond or alkylene of 1 to 6 carbon atoms; and
  each of W, Y and Z is independently hydrogen, fluoro, chloro, bromo, trifluoromethyl, methyl, ethyl, propyl, isopropyl, methoxy, ethoxy, propoxy, isopropoxy or nitro.

5. A compound according to claim 1 and having the formula:

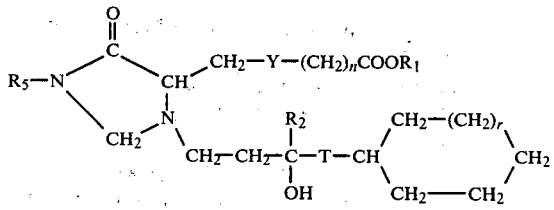

the pharmaceutically acceptable acid addition salt thereof, and the alkali metal, alkaline earth metal, ammonium and substituted ammonium salt when $R^1$ is hydrogen
wherein
  Y, $R_1$ and $R_5$ are as therein defined;
  n is 2, 3 or 4;
  $R_2$ is hydrogen, methyl, ethyl or phenyl;
  T is a carbon-carbon bond or alkylene of 1 to 6 carbon atoms; and
  r is 0, 1, 2 or 3.

6. A compound according to claim 1 wherein n is 3.

7. A compound according to claim 1 wherein Y is —$CH_2CH_2$—.

8. A compound according to claim 1 wherein $R_1$ is hydrogen or alkyl of 1 to 6 carbon atoms.

9. A compound according to claim 1 wherein $R_2$ is hydrogen or alkyl of 1 to 4 carbon atoms.

10. A compound according to claim 1 wherein $R_3$ is hydroxy.

11. A compound according to claim 1 wherein $R_4$ is alkyl of 4 to 9 carbon atoms.

12. A compound according to claim 1 wherein $R_4$ is phenyl or phenylalkyl, said phenyl and phenylalkyl being unsubstituted or substituted by halo, trifluoromethyl, alkyl of 1 to 6 carbon atoms, alkoxy of 1 to 6 carbon atoms, or nitro.

13. A compound according to claim 1 wherein $R_4$ is unsubstituted alkyl or alkoxyalkyl of up to 9 carbon atoms or alkyl or alkoxy of up to 6 carbon atoms substituted with cycloalkyl or phenyl, said phenyl being unsubstituted or substituted with one or more members selected from the group consisting of halo, trifluoromethyl, alkyl of 1 to 6 carbon atoms, hydroxy, alkoxy of 1 to 6 carbon atoms and nitro.

14. A compound according to claim 2 wherein n is 3.

15. A compound according to claim 2 wherein Y is —$CH_2CH_2$—.

16. A compound according to claim 2 wherein $R_2$ is methyl.

17. A compound according to claim 2 wherein $R_4$ is n-pentyl, n-hexyl, n-heptyl.

18. A compound according to claim 17 wherein $R_4$ is hexyl.

19. A compound according to claim 2 wherein $R_4$ is hex-2-yl; 2-methylhex-2-yl; hept-2-yl; 2-methylhept-2-yl; oct-2-yl or 2-methyloct-2-yl.

20. A compound according to claim 2 wherein $R_5$ is methyl.

21. 1-(3'-hydroxy-3'-methyl-n-nonyl)-3-methyl-5-(6''-methoxycarbonyl-n-hexyl)-4-imidazolidone.

22. A compound according to claim 3 wherein $R_4$ is alkoxyalkyl of up to 9 carbon atoms.

23. A compound according to claim 4 wherein n is 3.

24. A compound according to claim 4 wherein Y is —$CH_2CH_2$—.

25. A compound according to claim 4 wherein $R_2$ is methyl.

26. A compound according to claim 4 wherein W and Y are each hydrogen.

27. A compound according to claim 4 wherein Y is a carbon-carbon bond or straight chained alkylene of 1 to 4 carbon atoms.

28. A compound according to claim 5 wherein n is 3.

29. A compound according to claim 5 wherein Y is —$CH_2CH_2$—.

30. A compound according to claim 5 wherein $R_2$ is methyl.

31. A compound according to claim 5 wherein T is a carbon-carbon bond or straight chained alkylene of 1 to 6 carbon atoms.

32. A compound according to claim 5 wherein r is 1.

33. A compound according to claim 1 wherein $R_2$ and $R_4$ taken together are alkylene of 4 to 7 carbon atoms.

34. A compound according to claim 33 wherein $R_2$ and $R_4$ taken together are pentamethylene.

35. A pharmaceutical composition comprising an amount of a compound according to claim 1 sufficient to effect a prostaglandin like response and a pharmaceutically acceptable carrier.

36. A method of effecting a prostaglandin like response in humans and domestic animals, which comprises the administration thereto of an effective amount of a compound according to claim 1.

* * * * *